US00PP21552P3

(12) United States Plant Patent
Testolin et al.

(10) Patent No.: US PP21,552 P3
(45) Date of Patent: Dec. 7, 2010

(54) KIWI PLANT NAMED 'SORELI'

(50) Latin Name: ***Actinidia chinensis* Planchon**
Varietal Denomination: Soreli

(75) Inventors: Raffaele Testolin, Udine (IT); Guido Cipriani, Faedis (IT)

(73) Assignee: Universita degli Studi di Udine, Udine (IT)

( * ) Notice: Subject to any disclaimer, the term of this patent is extended or adjusted under 35 U.S.C. 154(b) by 0 days.

(21) Appl. No.: 12/456,176

(22) Filed: Jun. 12, 2009

(65) Prior Publication Data

US 2009/0313732 P1 Dec. 17, 2009

(30) Foreign Application Priority Data

Jun. 16, 2008 (QZ) ..... PBR 2008/1319

(51) Int. Cl.
*A01H 5/00* (2006.01)

(52) U.S. Cl. ..... Plt./156

(58) Field of Classification Search ..... Plt./156
See application file for complete search history.

*Primary Examiner*—Annette H Para
(74) *Attorney, Agent, or Firm*—Michelle Bos

(57) ABSTRACT

A new female tetraploid kiwifruit plant, *Actinidia chinensis,* named 'Soreli'. The new variety results from a controlled cross made using tetraploid *A. chinensis* 'A137' as seed-parent and *A. chinensis* 'A134.41' as pollen donor. 'Soreli' bears single flowers; the fruit is large (118 g on average), oblong, circular in cross section with a reddish brown skin and a brilliant yellow flesh; core is small. Fruit taste sweet, acidity is low. Fruit are harvested earlier than both 'Jintao' and 'Hayward'. Bud break occurs 6 and 8 days before 'Jintao' and 'Hayward' respectively and flowering time occurs 2 and 9 days before 'Jintao' and 'Hayward' respectively in Udine (46° 02' N, 13° 13' E; 88 m asl) where the comparative observations were carried out. Fruit has medium storage life (up to 3-4 months).

7 Drawing Sheets

Genus and species: *Actinidia chinensis* Planchon.
Variety denomination: 'Soreli'.

BACKGROUND OF THE NEW VARIETY

The invention relates to a new variety of kiwifruit plant (*Actinidia chinensis* Planchon) named 'Soreli.' The new variety produces fruit for the fresh market, as well as for food products such as juice, jam, wine, spirits, fortified food, nutraceuticals and beauty products.

'Soreli' originated in the course of a plant breeding program initiated in May 1997 at the University of Udine, Italy by crossing 3 female by 6 male breeding lines, according to a North Carolina Model 2 cross design.

Seeds of fruit obtained from the controlled crosses were extracted in the winter of 1997-1998 and sowed in the spring of 1998. Plants were transplanted in the open field in the winter of 1998-1999. Some 108 seedlings were grown for each controlled cross.

Fruits were observed beginning in 2002, and after several years of field observations, storage and sensory evaluation, 'Soreli' was selected from the cross family Ac171 (A137× A134.41) with the code Ac171.76.

Field trials in different growing areas started in 2005 with grafted plants. Propagation was also successfully tested through rooted cuttings and tissue culture, and observations done on regenerated plants bearing fruit confirmed that the new material comes true to the original genotype.

The original plant is still maintained in collection at the experimental farm of University of Udine.

BRIEF SUMMARY OF THE INVENTION

'Soreli' is a new kiwifruit plant obtained as the result of a controlled cross made using the female *A. chinensis* 'A137' as seed-parent and the male *A. chinensis* 'A134.41' as pollen donor. 'A137' has unknown parentage and 'A134.41' originated from a selection of seeds introduced from the Guangdong province of China in 1993. Both parents ('A137' and 'A134.41') are unpatented breeding lines held at the *Actinidia* germplasm repository of the University of Udine, Italy.

'Soreli' is different from all kiwifruit varieties described up to now in the western literature and in the Chinese literature for which illustrations of the fruit and an English caption are available. It is distinguishable from the most similar variety ('Jintao', not patented) by the following characteristics:

1. Larger, more rounded fruit.
2. More brilliant brown skin colour.
3. Slightly earlier bud break and bloom dates.
4. Earlier maturity date.

DESCRIPTION OF THE DRAWINGS

The illustrations include photographs of 'Soreli' and of 'Jintao', the commercial variety that most resembles 'Soreli' and to which 'Soreli' is compared in the following botanical description.

DETAILED BOTANICAL DESCRIPTION

Figure 1A:
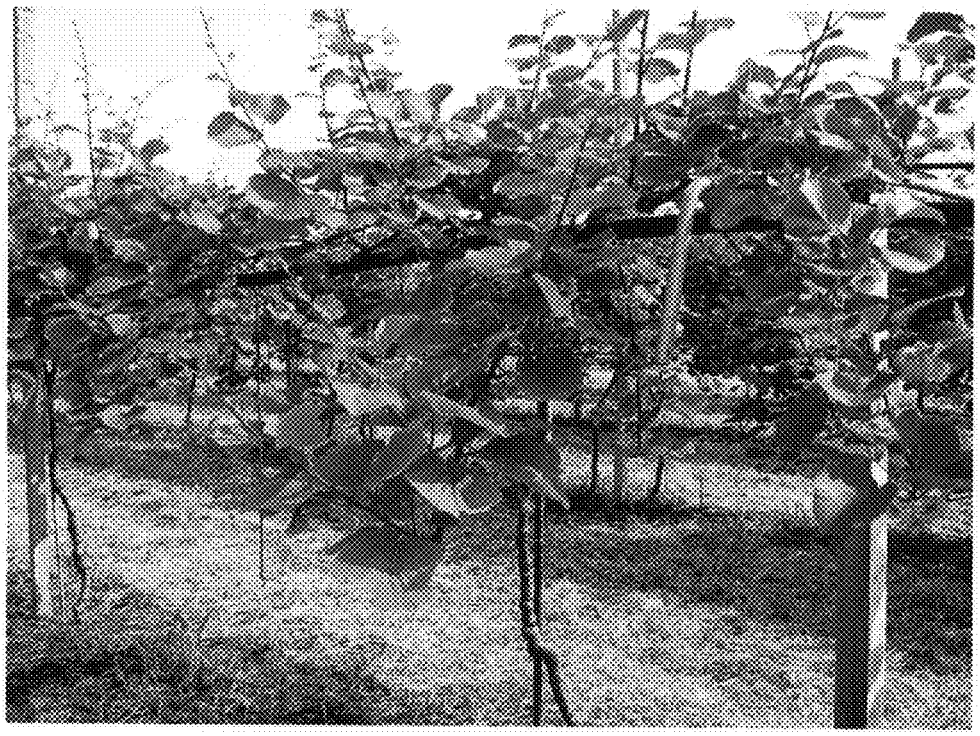
FIGS. 1*a* and 1*b* show the whole plant of 'Soreli' and 'Jintao', respectively.
Figure 1B:
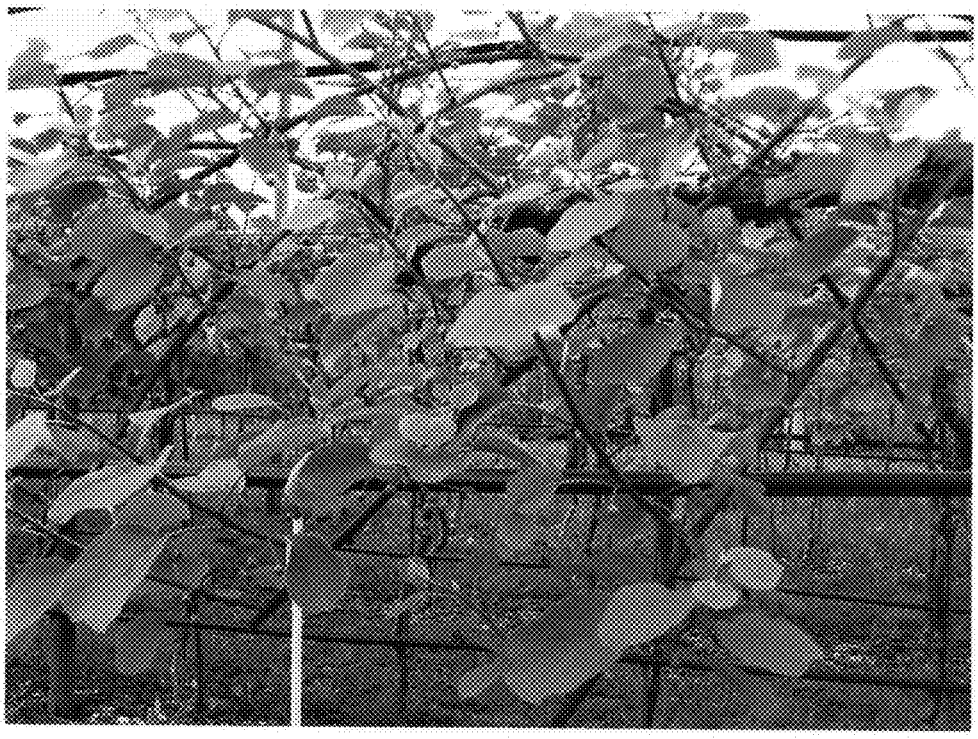
Figure 2A:
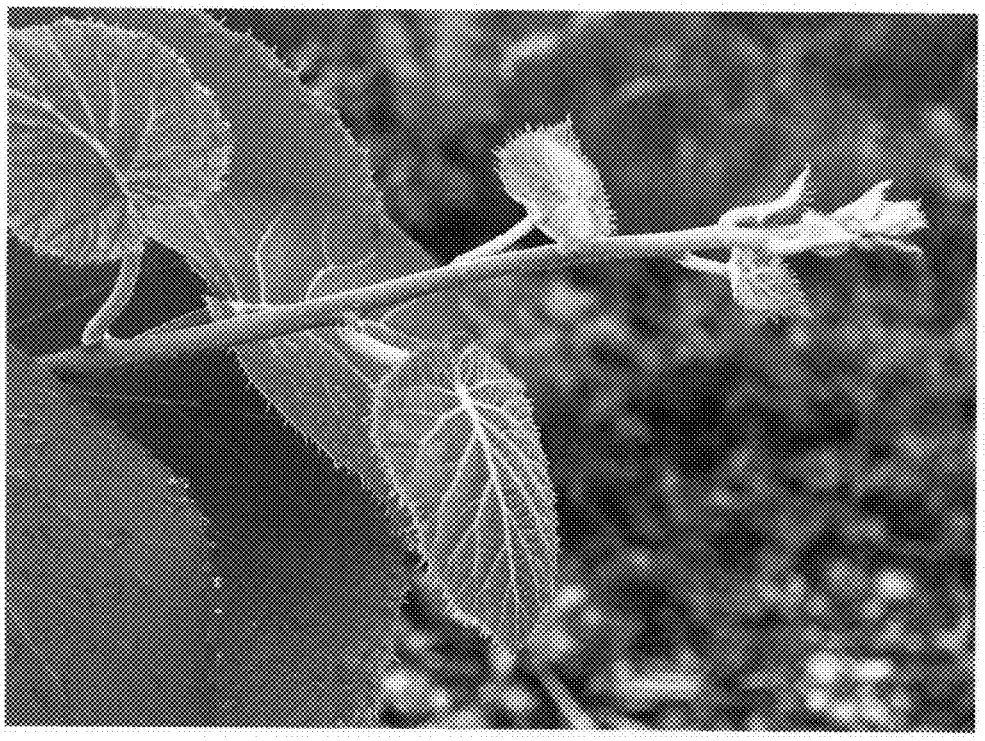
FIGS. 2*a* and 2*b* show the shoot of 'Soreli' and 'Jintao', respectively.
Figure 2B:
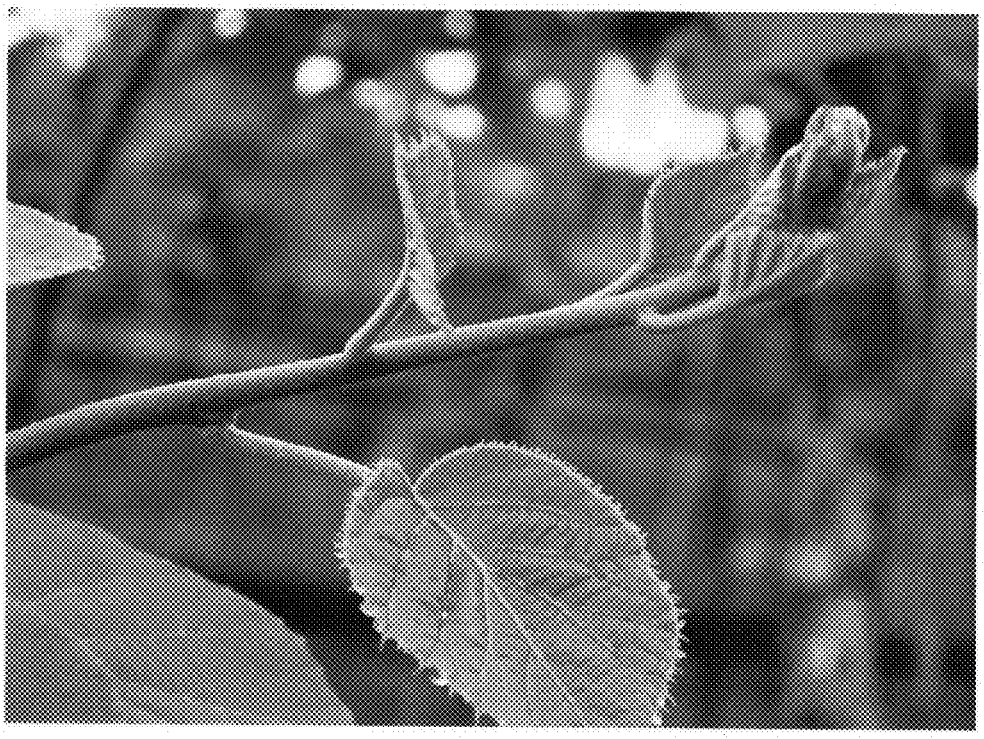
Figure 3A:
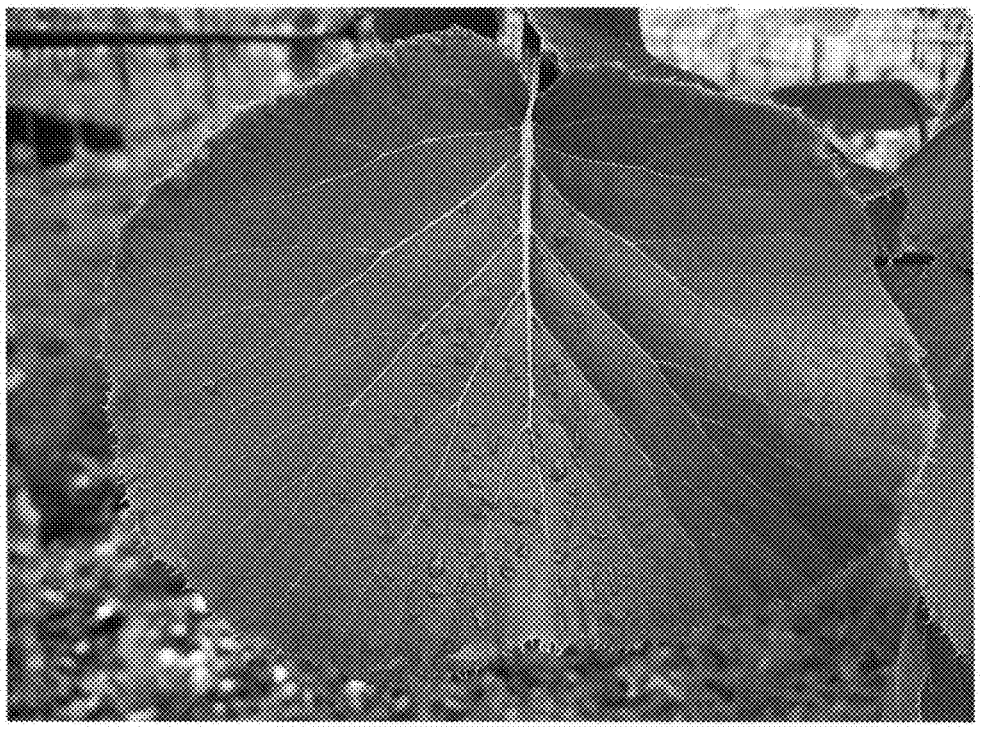
FIGS. 3*a* and 3*b* show the leaves of 'Soreli' and 'Jintao', respectively.
Figure 3B:
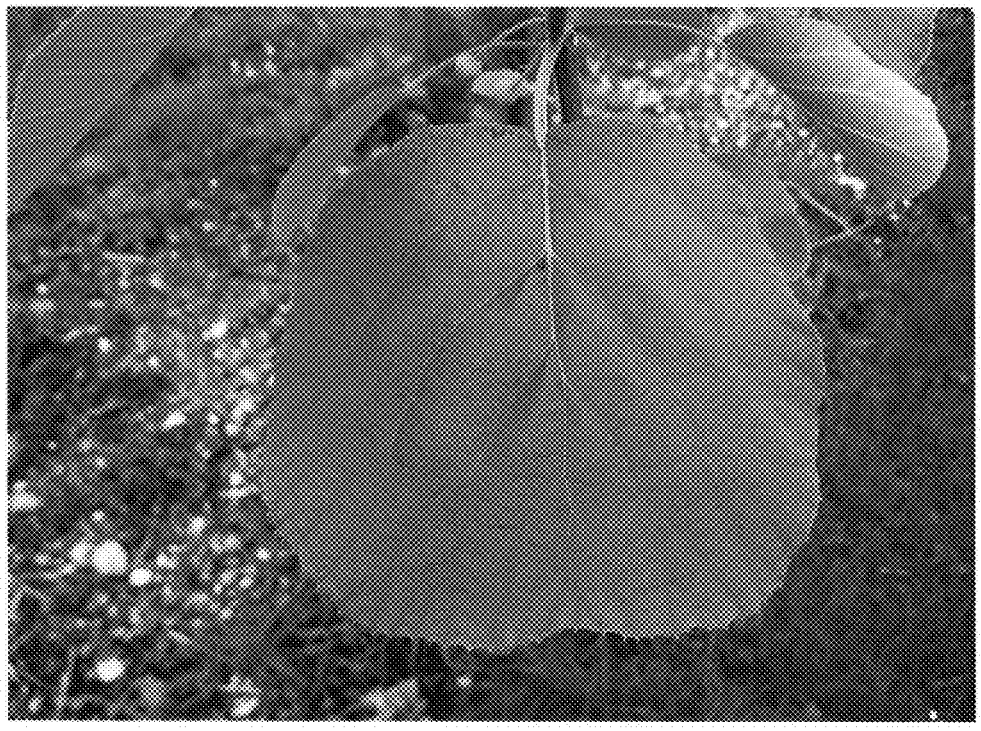
Figure 4A:
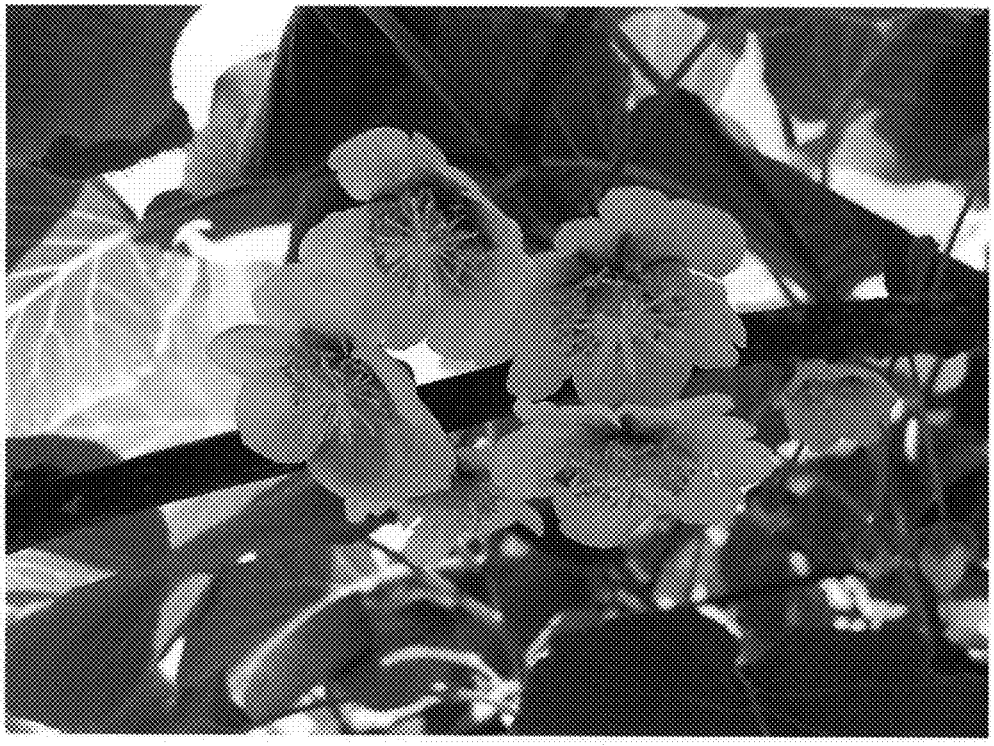
FIGS. 4*a* and 4*b* show flowers on the vine of 'Soreli' and 'Jintao', respectively.
Figure 4B:
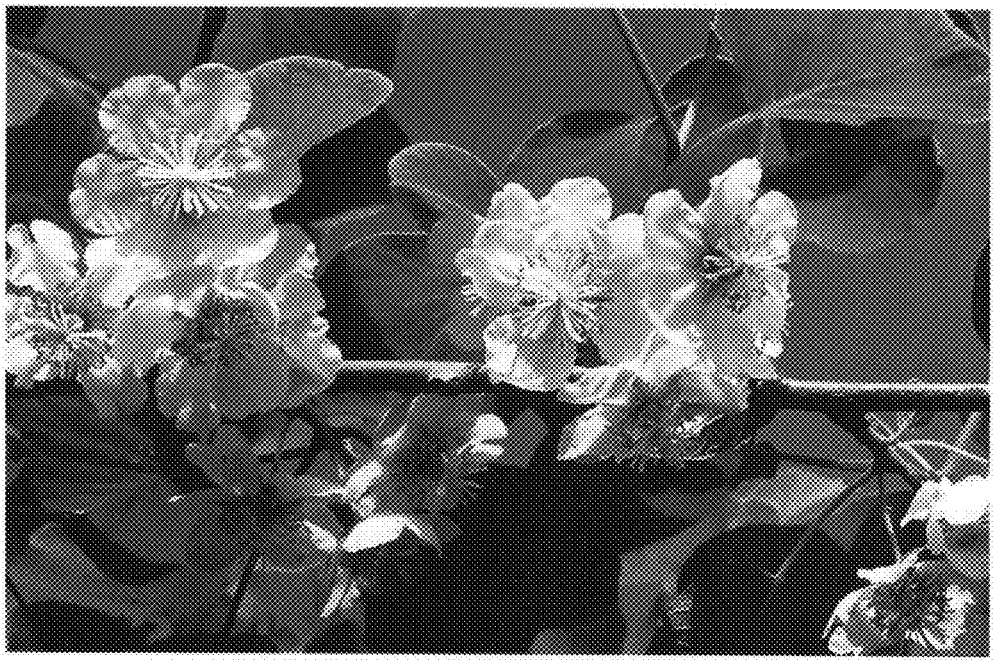
Figure 5A:
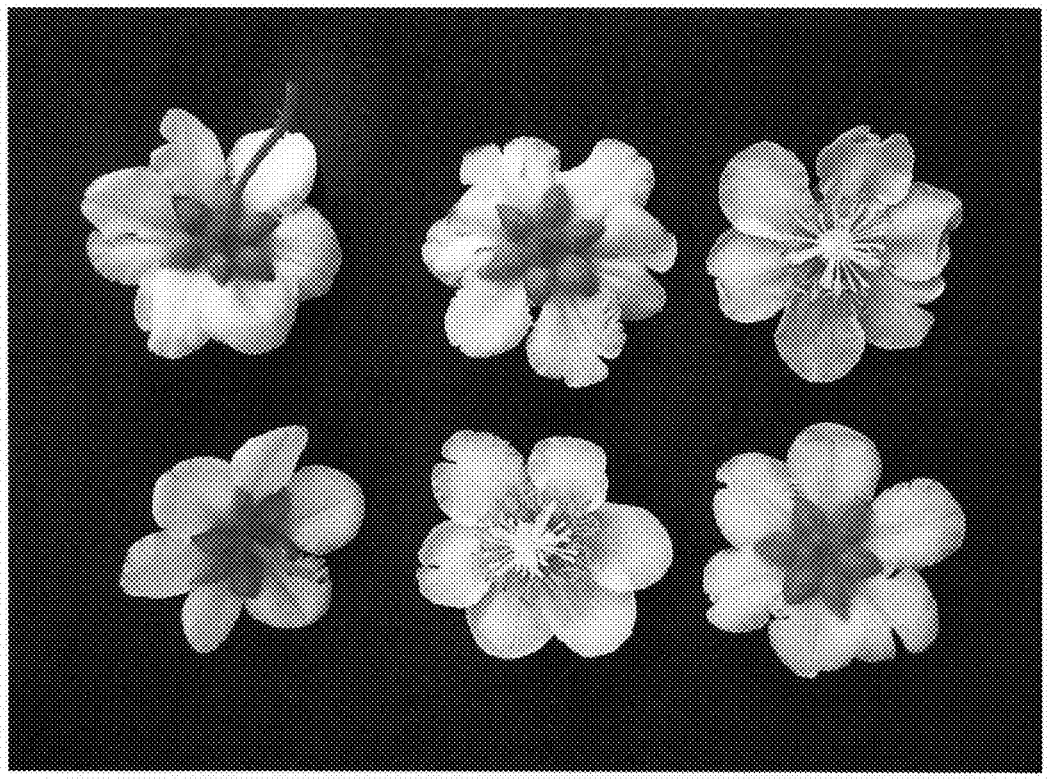
FIGS. 5*a* and 5*b* show flowers of 'Soreli' and 'Jintao', respectively.
Figure 5B:
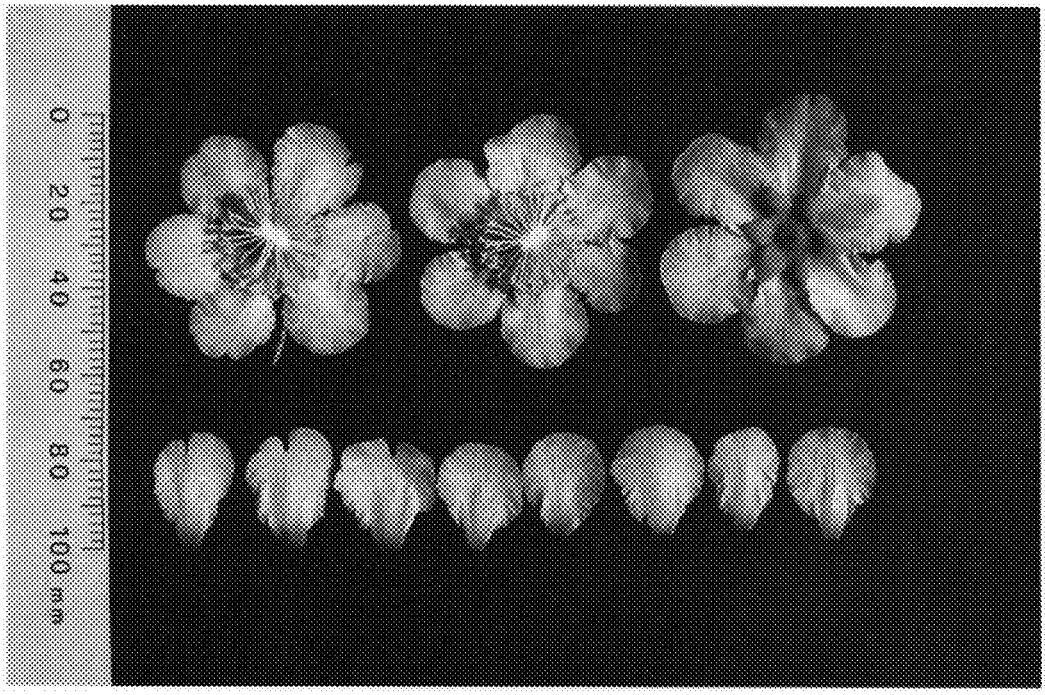
Figure 6A:
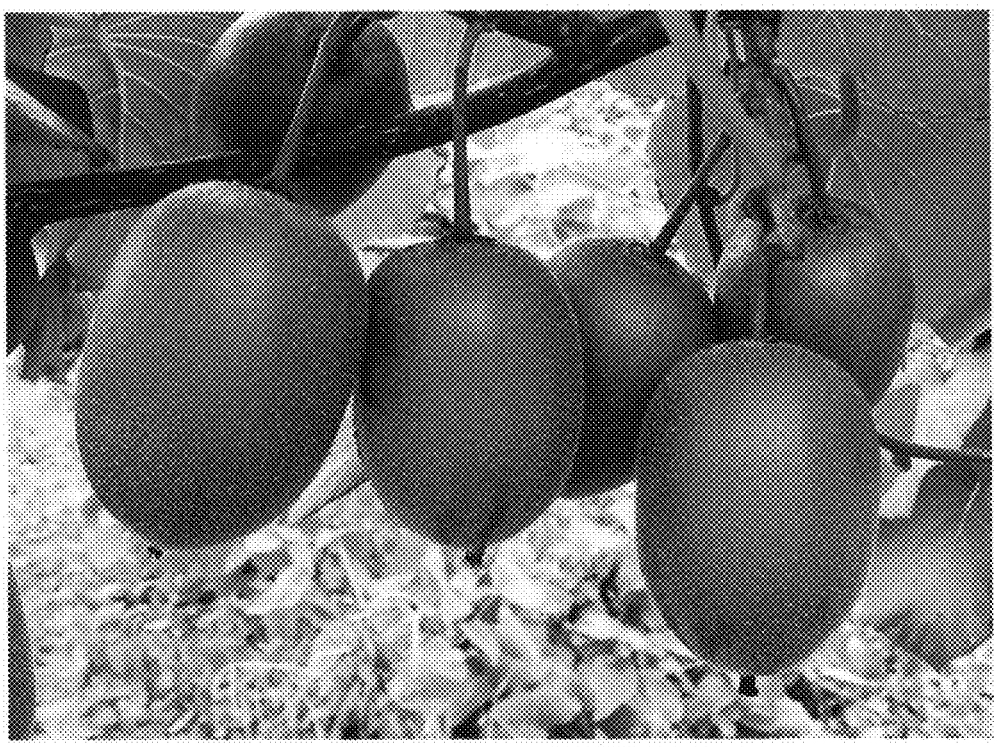
FIGS. 6*a* and 6*b* show fruit on the vine of 'Soreli' and 'Jintao', respectively.
Figure 6B:
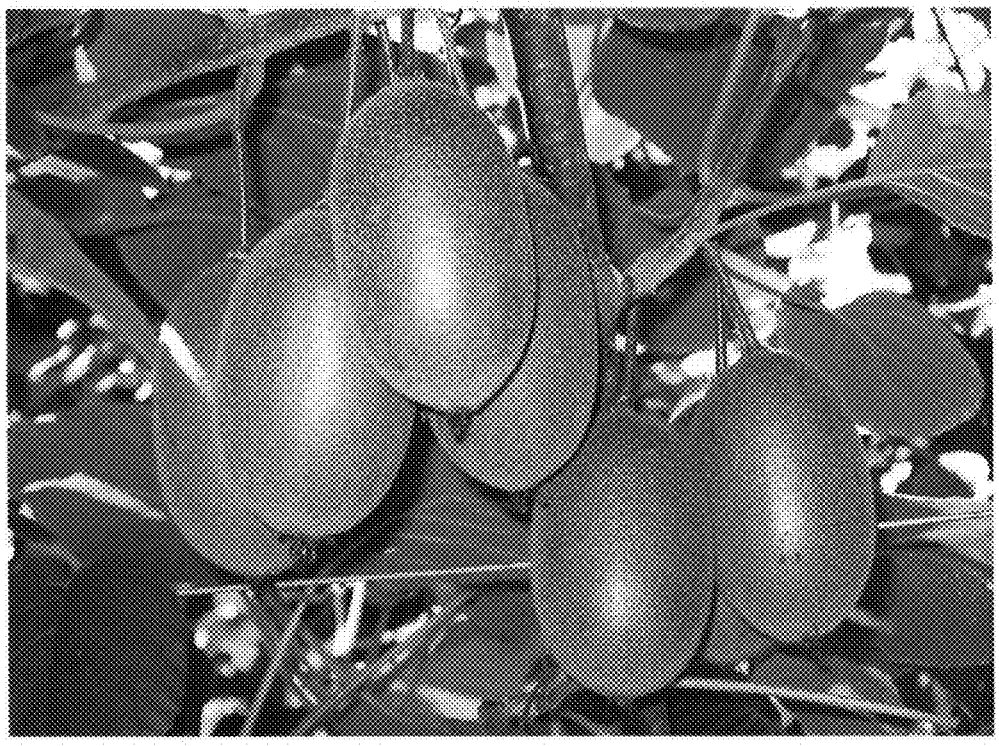
Figure 7A:
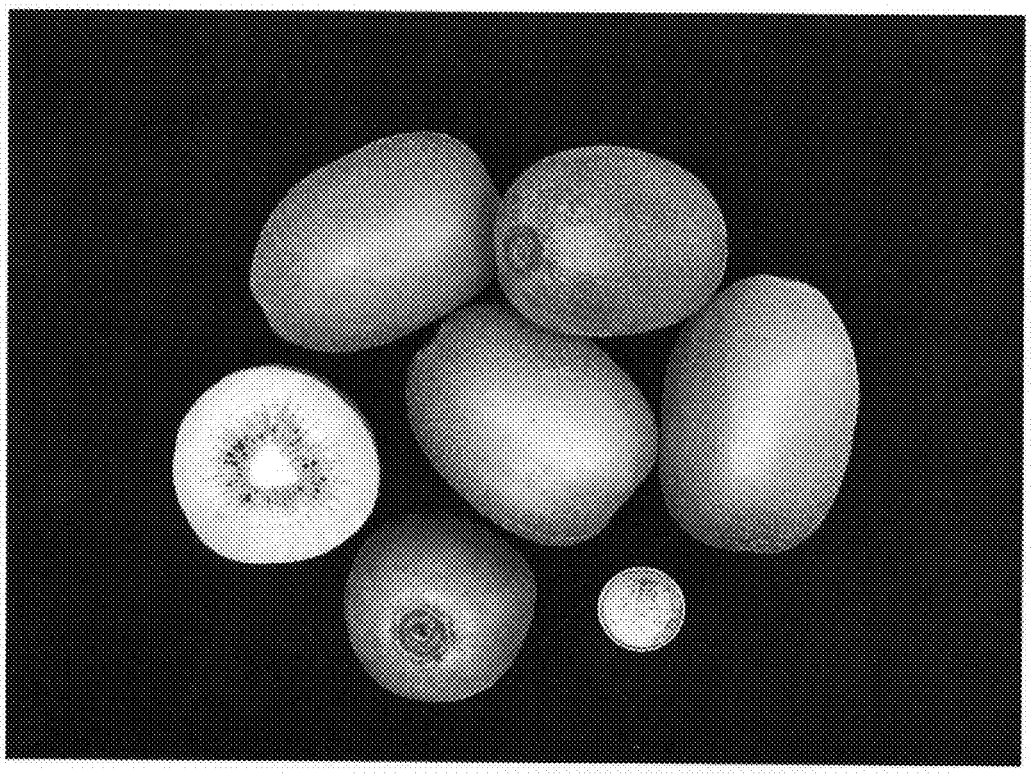
FIGS. 7*a* and 7*b* show fruit of 'Soreli' and 'Jintao', respectively, in profile and in cross section.
Figure 7B:
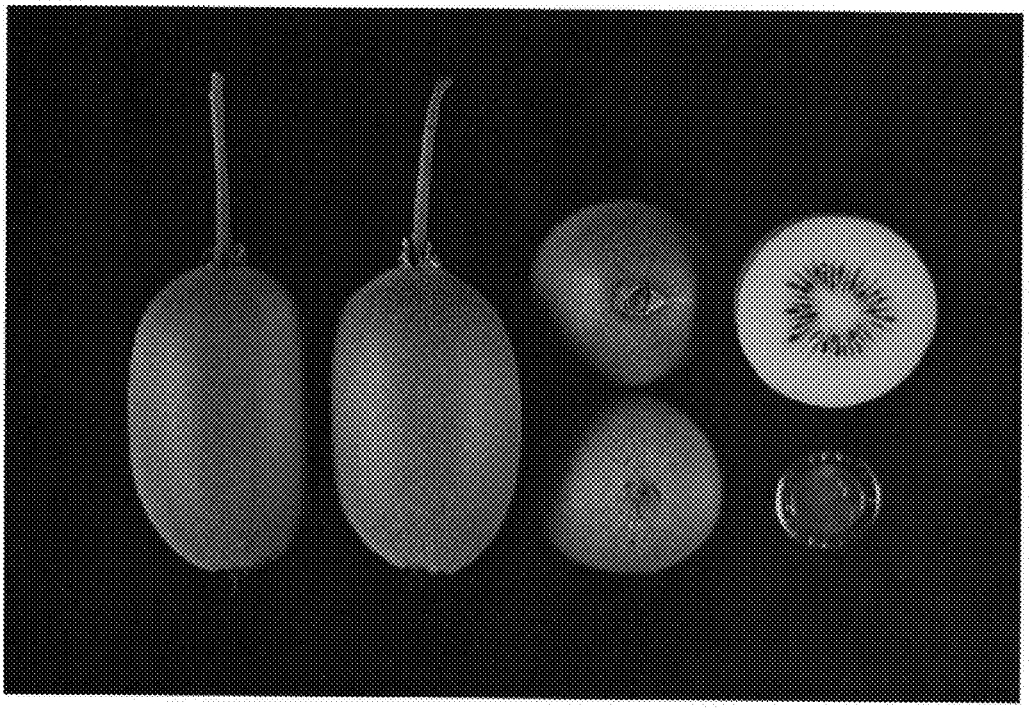

The following is a detailed botanical description of 'Soreli,' based on observations made during the 2009 growing season at Udine, Italy. It should be understood that the botanical and analytical characteristics described will vary somewhat depending upon cultural practices and climatic conditions, and can vary with location and season. Color descriptions are made with reference to The Royal Horticultural Society Colour Chart. Quantified measurements are expressed as an average of measurements taken from a number of individual plants of the new variety. The measurements of any individual plant, or any group of plants, of the new variety may vary from the stated average.

Descriptors and terminology are in accordance with the UPOV technical guidelines for kiwifruit, adopted by the European Community Plant Variety Office in its technical questionnaire (http://www.cpvo.europa.eu/). Traits of 'Jintao' are reported for comparison in the last column when significantly different.

TABLE 1

| | 'Soreli' | 'Jintao' |
|---|---|---|
| Plant: sex | female | |
| Ploidy | tetraploid | |
| Plant: vigor | weak | medium |
| Young shoot: hairiness | present | |
| Young shoot: density of hair | medium | dense |
| Young shoot: type of hairiness | velutinous | downy |
| Young shoot: anthocyanin coloration of growing tip | absent/very weak | |
| Stem: coloration of leaf axil | purple brown 200B | |
| Stem: diameter | 12.8 mm | |
| Stem: length | 29.8 mm | |
| Stem: dormant bud diameter | 8.1 mm | |
| Stem: color on upper side of shoot | purple brown 200B | |
| Stem: colour of shoot on sunny side | purple brown 200B | red brown |
| Stem: roughness of bark | smooth | |
| Stem: hairiness | absent | |
| Stem: size of lenticels | narrow & long, 5.3 mm | variable |
| Stem: number of lenticels | Few, 6.8 per $cm^2$ | |
| Stem: colour of lenticels | White 155A | |
| Stem: size of bud support | medium to large, 12.4 mm | |
| Stem: presence of bud cover | absent | |
| Stem: size of hole in bud cover | Large, 5.2 mm | |
| Stem: leaf scar | shallow | deep |
| Leaf blade: shape | very broad ovate | |
| Leaf blade: length | 168 mm | |
| Leaf blade: width | 174 mm | |
| Leaf blade: shape of apex | acuminate | |
| Leaf blade: arrangement of basal lobes | slightly overlapping | touching each other |
| Leaf blade: hair on upper side | absent/very sparse | |
| Leaf blade: hair on lower side | medium | |
| Leaf blade: colour of upper side | green 137A | |
| Leaf blade: colour of lower side | green 139C | |
| Petiole: length | 101 mm | |
| Petiole: diameter | 5 mm | |
| Petiole: color | greyed-purple 185B | |
| Petiole: anthocyanin coloration of upper side | strong | weak |
| Inflorescence: predominant no. of flowers | 1 | |
| Flower stalk: length | Long, 101 mm | |
| Flower: number of sepals | >5 | |

TABLE 1-continued

| | 'Soreli' | 'Jintao' |
|---|---|---|
| Sepal: general colour | Green 141D | |
| Sepal: length | 9.2 mm | |
| Sepal: diameter | 4.8 mm | |
| Flower: diameter | Large, 37.5 mm | |
| Flower: arrangement of petals | touching | |
| Petal: length | 18.7 mm | |
| Petal: width | 13.4 mm | |
| Petal: curvature of apex | weakly expressed | |
| Petal: type of coloration (adaxial side) | single-coloured | bicoloured |
| Petal: main colour on adaxial side | yellowish white 155D | white |
| Petal: different shades of colour | absent | |
| Petal: distribution of colour | lighter towards apex | |
| Anther: colour | Yellow 6A | |
| Styles: quantity | many | |
| Styles: attitude | both erect and horizontal | |
| Fruit: size | large | medium |
| Fruit: length | 58 mm | |
| Fruit: diameter | 45 mm | |
| Fruit: general shape | oblong | |
| Fruit: shape in cross section (at median) | circular | |
| Fruit: general shape of stylar end | slightly depressed | flat |
| Fruit: presence of calyx ring | weakly expressed | |
| Fruit: shape of shoulder at stalk end | squared | |
| Fruit: length of stalk | Long, 47 mm | |
| Fruit: diameter of stalk | 3 mm | |
| Fruit: persistence of sepals | absent | |
| Fruit: colour of skin | greyed-orange 172A | brown |
| Fruit: hairiness of skin | present | |
| Fruit: density of hair | very sparse | |
| Fruit: distribution of hairs | evenly spread | |
| Fruit: colour of hairs | greyed-orange 163A | |
| Fruit: adherence of hairs to skin (when rubbed) | strong | |
| Fruit: colour of skin at maturity for consumption | greyed-orange 172A | brown |
| Fruit: colour of lenticels | Greyed-orange 166C | |
| Fruit: length of lenticels | 0.8 mm | |
| Fruit: width of lenticels | 0.5 mm | |
| Fruit: colour of outer pericarp | yellow 4A | |
| Fruit: colour of inner pericarp (locules) | yellow 12A | |
| Fruit: diameter of core relative to fruit | Small | |
| Fruit: general shape of core (in cross section) | Oblate | |
| Fruit: colour of core | yellow white 155C | |
| Fruit: sweetness | High | |
| Fruit: acidity | Low | medium |
| Time of vegetative bud burst | medium | |
| Time of beginning of flowering | Medium | |
| Time of maturity for harvest | Early | Medium |
| Fruit storage life | medium (up to 3 to 4 months) | |

Information reported below relates to observations made at the experimental farm of the University of Udine (46° 02' N, 13° 13' E; 88 m asl) during the years 2002-2008 (data are means±std dev).

TABLE 2

| Trait | 'Soreli' | 'Jintao' | 'Hayward' (not patented) |
|---|---|---|---|
| bud break | March 15 ± 13 | March 21 ± 8 | March 23 ± 8 |
| flowering time (50% open flowers) | May 12 ± 9 | May 14 ± 8 | May 23 ± 8 |
| harvesting time (>7% SSC) (*) | October 10 ± 8 | October 11 ± 5 | November 02 ± 7 |

TABLE 2-continued

| Trait | 'Soreli' | 'Jintao' | 'Hayward' (not patented) |
|---|---|---|---|
| fruit weight (g) at harvest | 118 ± 13 | 95 ± 6 | 109 ± 6 |
| fruit firmness (kg/cm2) at harvest | 4.8 ± 1.9 | 6.8 ± 0.5 | 8.2 ± 0.8 |
| fruit SSC (%) at harvest | 11.1 ± 1.9 | 8.1 ± 0.7 | 6.7 ± 0.5 |
| fruit SSC at maturity | 14.5 ± 1.8 | 15.3 ± 0.9 | 13.4 ± 1.3 |

(*) Hayward was harvested at lower SSC content (>6.2 %) because of the risk of frost

We claim:

1. We claim a new and distinct kiwifruit plant of the species *A. chinensis* (tetraploid) substantially as described and illustrated herein, characterized by yellow sweet flesh and brilliant brown fruit skin, large fruit size, oblong fruit shape with a slightly depressed stylar end.

* * * * *